(12) United States Patent
Rao et al.

(10) Patent No.: US 6,255,498 B1
(45) Date of Patent: Jul. 3, 2001

(54) METHOD FOR SYNTHESIZING DIARYL-SUBSTITUTED HETEROCYCLIC COMPOUNDS, INCLUDING TETRAHYDROFURANS

(75) Inventors: Alla Verkata Rama Rao, Hyderabad (IN); Mukund S. Chorghade, Wellesley, MA (US); Amin ul Islam, Hyderabad (IN); Vemuri Venkata Kiran Rao, Andhra Pradesh (IN); Anegondi Sreenivasa Prasad, Hyderabad (IN)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/173,918

(22) Filed: Oct. 16, 1998

(51) Int. Cl.$^7$ .................................................. C07D 307/02
(52) U.S. Cl. .......................... 549/429; 549/80; 546/268.1
(58) Field of Search ................... 549/80, 429; 546/268.1

(56) References Cited

U.S. PATENT DOCUMENTS

| | | | |
|---|---|---|---|
| 5,037,853 | 8/1991 | Brooks et al. | 514/595 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 514/231.5 |
| 5,187,192 | 2/1993 | Brooks et al. | 514/445 |
| 5,288,751 | 2/1994 | Brooks et al. | 514/438 |
| 5,326,787 | 7/1994 | Brooks et al. | 514/507 |
| 5,358,938 | 10/1994 | Cai et al. | 514/231.5 |
| 5,434,151 | 7/1995 | Cai et al. | 514/231.5 |
| 5,463,083 | 10/1995 | Biftu et al. | 549/71 |
| 5,530,141 | 6/1996 | Shen et al. | 549/39 |
| 5,543,531 | 8/1996 | Funfschilling et al. | 549/62 |
| 5,639,782 | 6/1997 | Shen et al. | 574/440 |
| 5,681,966 | 10/1997 | Cai et al. | 549/65 |
| 5,703,093 | 12/1997 | Cai et al. | 514/473 |
| 5,741,809 | 4/1998 | Biftu et al. | 514/428 |
| 5,750,565 | 5/1998 | Cai et al. | 514/473 |
| 5,756,768 | 5/1998 | Kanou et al. | 549/66 |
| 5,780,503 | 7/1998 | Biftu et al. | 514/471 |
| 5,792,776 | 8/1998 | Biftu et al. | 514/303 |
| 5,856,323 | 1/1999 | Cai et al. | 514/231.5 |

FOREIGN PATENT DOCUMENTS

WO 92/15294   9/1992   (WO) .
WO 94/01430   1/1994   (WO) .
WO 94/06790   3/1994   (WO) .
WO 95/18610   7/1995   (WO) .
WO 96/00212   1/1996   (WO) .

*Primary Examiner*—Amelia Owens
(74) *Attorney, Agent, or Firm*—Peter F. Corless; Christine C. O'Dav; Edwards & Angell LLP

(57) ABSTRACT

A method is provided for synthesizing diaryl-substituted heterocyclic compounds, particularly 2,5-diaryl-substituted tetrahydrofurans and tetrahydrothiophenes. Methods for synthesizing starting materials and intermediates are provided as well. An important application of the invention is in the synthesis of CMI-392, (±) trans-2-[5-(N'-methyl-N'-hydroxyureidyl-methyl)-3-methoxy-4-p-chlorophenylthioethoxyphenyl]-5-(3,4,5-thrimethoxyphenyl)-tetrahydrofuran, a highly effective agent in treating inflammatory and immune disorders. The invention also encompasses novel compounds useful as starting materials and intermediates in the synthetic processes disclosed.

16 Claims, 6 Drawing Sheets

112

113

114

115 (crude CMI-392)

isopropanol/
n-hexane 116 (pure crystalline CMI-392)

CMI-392

METHOD FOR SYNTHESIZING DIARYL-SUBSTITUTED HETEROCYCLIC COMPOUNDS, INCLUDING TETRAHYDROFURANS

TECHNICAL FIELD

The present invention relates generally to the field of synthetic organic chemistry, and more particularly relates to a novel method for synthesizing diaryl-substituted heterocyclic compounds useful for treating inflammatory and immune disorders. The invention also pertains to novel chemical compounds useful as intermediates in the presently disclosed synthetic methods.

BACKGROUND

Allergy, asthma, autoimmune disorders and tissue injury are known to induce the release of lipid mediators, leukotrienes generated by the 5-lipoxygenase ("5-LO") pathway, and platelet activating factor ("PAF", 1-O-alkyl-2-acetyl-sn-glycerol-3-phosphoryl choline) from leukocytes. Leukotrienes and PAF trigger the major symptoms of inflammatory diseases: bronchoconstriction, cellular infiltration, swelling, congestion and pain. Recent efforts in identifying and developing effective agents to treat inflammatory and immune disorders have led to the synthesis of a family of important compounds, described in detail in U.S. Pat. No. 5,434,151 to Cai et al. Those compounds reduce damage arising from an inflammatory or immune response by acting as receptor antagonists of platelet activating factor by inhibiting the activity of 5-lipoxygenase, or both. As described in detail in the aforementioned patent, the compounds are 2,5-diaryl tetrahydrothiophenes, tetrahydrofurans, and pyrrolidines, 1,3-diaryl cyclopentanes, and 2,4-diaryl tetrahydrothiophenes, tetrahydrofurans and pyrrolidines. An exemplary compound is (±) trans-2-[5-(N'-methyl-N'-hydroxyureidylmethyl)-3-methoxy-4-p-chlorophenylthioethoxy-phenyl]-5-(3,4,5-thrimethoxyphenyl)tetrahydrofuran, sometimes referred to herein as "CMI-392" and shown in the following formula:

Previously, the only known process for synthesizing and purifying CMI-392—as disclosed in U.S. Pat. No. 5,434,151 to Cai et al.—resulted in a waxy, low melting point solid that proved to be difficult to work with and sensitive to heat, light and moisture. In co-pending patent application Ser. No. 09/173,903 entitled "Topical Pharmaceutical Formulations Useful to Treat Inflammatory and Immune Disorders," filed on Oct. 16, 1998, a method is disclosed for preparing CMI-392 and analogs thereof in a crystalline form that is stable to heat, light and moisture. That method, which involves recystallization in isopropyl alcohols, optionally combined with n-hexane, is extraordinarily valuable insofar as a variety of different types of pharmaceutical formulations may now be prepared, aqueous vehicles may be used, and far fewer precautions need to be taken with respect to possible exposure to slightly elevated temperatures and light. Nevertheless, there remains a need for an improved synthetic route to CMI-392 and analogs thereof, preferably in crystalline form, which avoids harsh reagents and extreme reaction conditions, and provides the desired product in high yield. The present invention is directed to such a synthesis.

SUMMARY OF THE INVENTION

Accordingly, it is a primary object of the invention to address the above-mentioned need in the art by providing a new method for synthesizing CMI-392 and structurally similar diaryl-substituted heterocycles, particularly 2,5-diaryl-substituted tetrahydrofurans and 2,5-diaryl-substituted tetrahydrothiophenes.

It is another object of the invention to provide methods for synthesizing starting materials and intermediates useful for preparing diaryl-substituted heterocycles such as 2,5-diaryl-substituted tetrahydrofurans and tetrahydrothiophenes.

It is still another object of the invention to provide novel compounds useful as starting materials and/or intermediates in the synthesis of diaryl-substituted heterocycles such as 2,5-diaryl-substituted tetrahydrofurans and 2,5-diaryl-substituted tetrahydrothiophenes.

Additional objects, advantages and novel features of the invention will be set forth in part in the description which

CMI-392

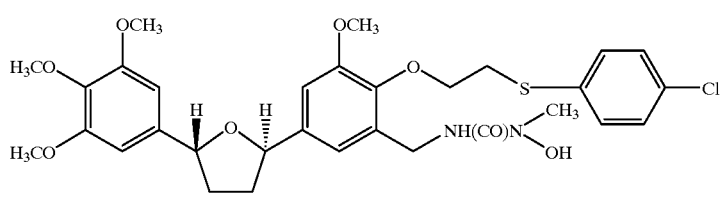

CMI-392, a compound that, uniquely, is both a 5-LO inhibitor and a PAF receptor antagonist, has proved to be an extremely effective agent for treating inflammatory and immune disorders, as have the other compounds set forth in the Cai et al. patent. The compounds have been found to be particularly useful in treating psoriasis and atopic dermatitis, both chronic inflammatory skin disorders affecting millions of people. A number of pharmaceutical compositions containing these drugs have been proposed and prepared. However, there remains a need for an improved synthetic route to prepare these valuable agents.

follows, and in part will become apparent to those skilled in the art upon examination of the following, or may be learned by practice of the invention.

DETAILED DESCRIPTION OF THE INVENTION

Figure 1A:
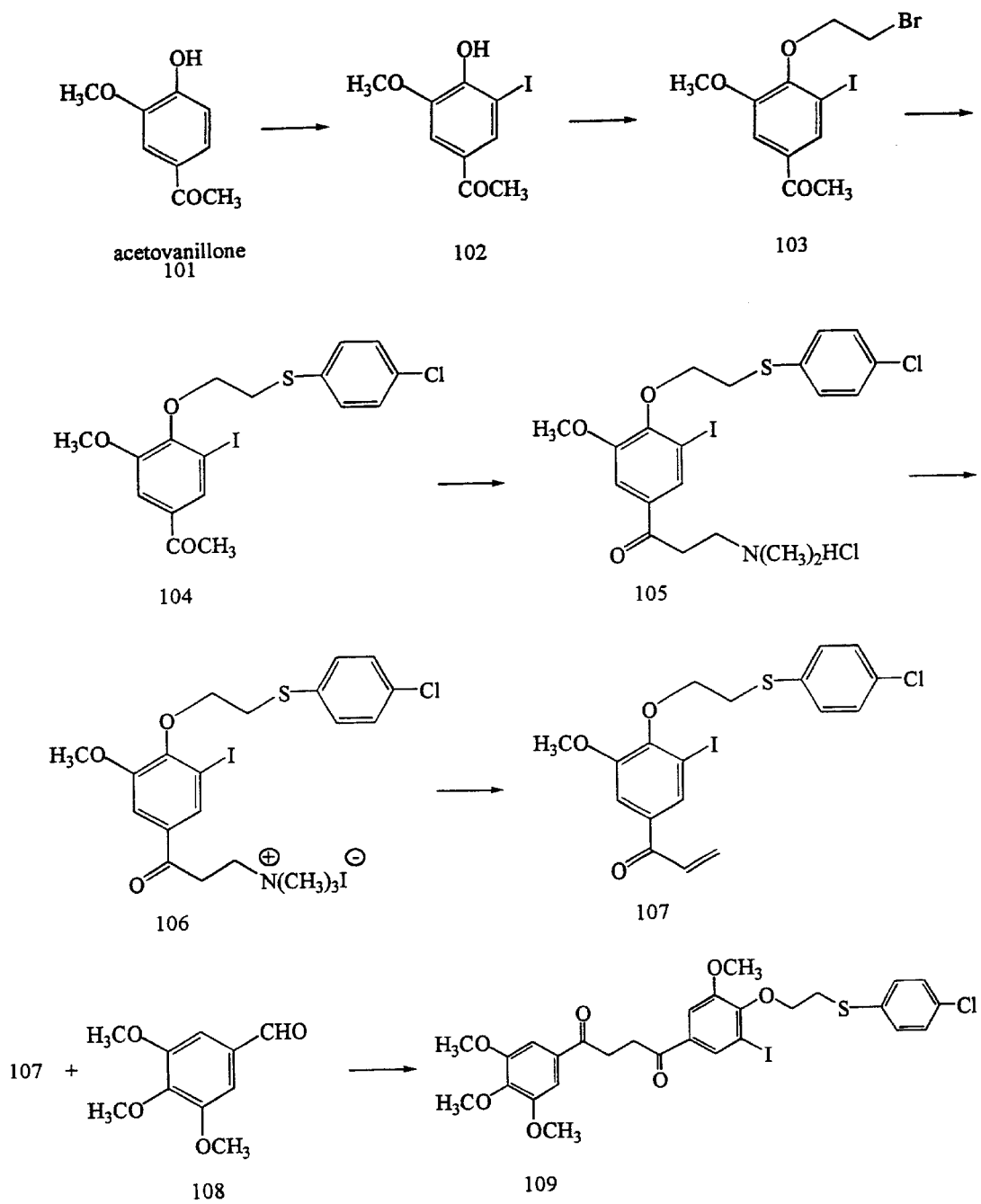
FIGS. 1a–1c schematically illustrate a method for synthesizing crystalline CMI-392 using acetovanillone as a starting material, as described in the Example.

Before the present invention is disclosed and described in detail, it is to be understood that this invention is not limited to specific starting materials, reagents, reaction conditions, or the like, as such may vary. It is also to by understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an active agent" includes mixtures of active agents, reference to "a solvent" includes mixtures of two or more solvents, and the like.

With respect to the description of chemical structures and substituents contained therein, the following definitions are applicable:

The term "alkyl" as used herein, unless otherwise specified, refers to a saturated straight chain, branched or cyclic hydrocarbon group of 1 to 10 carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term "alkenyl" as used herein, unless otherwise specified, refers to a branched, unbranched or cyclic (in the case of $C_5$ and $C_6$) hydrocarbon group of 2 to 10 carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl.

The term "alkynyl" as used herein, unless otherwise specified, refers to a branched or unbranched hydrocarbon group of 2 to 10 carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl.

The term "lower alkylamino" as used herein, and unless otherwise specified, refers to an amino group that has one or two alkyl substituents.

The term "aryl" as used herein, and unless otherwise specified, refers to phenyl or substituted phenyl, wherein the substituent is halo or lower alkyl.

The term "halo" is used in its conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The terms "heterocycle" or "heteroaromatic" as used herein, and unless otherwise specified, refer to an aromatic moiety that includes at least one sulfur, oxygen or nitrogen atom in the aromatic ring. Such moieties include, but are not limited to, pyrryl, furyl, pyridyl, 2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl and isoxazolyl.

The term "aralkyl" refers to an aryl group with an alkyl substituent.

The term "alkaryl" refers to an alkyl group that has an aryl substituent.

"Optional" or "optionally" means that the subsequently described circumstances may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

In a first embodiment of the invention, a method is provided for synthesizing a diaryl-substituted heterocyclic compound, particularly of a diaryl-substituted tetrahydrofuran or tetrahydrothiophene, from an aromatic aldehyde or thioaldehyde and an aromatic vinyl ketone or thioketone. The synthetic method is straightforward, makes use of mild reagents and reaction conditions, and provides the desired product in a relatively high yield. CM-392 and analogs thereof may be synthesized, in isomerically pure form, using the presently disclosed and claimed methodology.

In a first embodiment, then, a method is provided for synthesizing a compound having the structural formula (I)

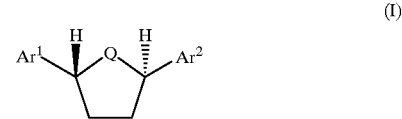

(I)

in which Q is O or S and $Ar^1$ and $Ar^2$ are selected from the group consisting of aryl, aralkyl, heteroaryl and heteroaralkyl, optionally substituted with 1 to 3 substituted. Preferably, $Ar^1$ and $Ar^2$ are independently selected from the group consisting of phenyl and pyridinyl, either unsubstituted or substituted at least one substituents selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —$CN$, wherein $R^1$, and $R^2$ and $R^3$ are independently hydrogen, alkyl or aryl, m is 1, 2 or 3, and n is an integer in the range of 1 to 6. The method comprises catalytically coupling the aldehyde or thioaldehyde (II)

(II)

to the vinyl ketone or thioketone (III)

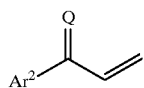
(III)

under reaction conditions effective to produce the diaryl-substituted dione or dithione (IV)

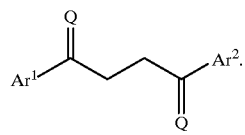
(IV)

The reaction involves admixing reactants (II) and (III) in a suitable solvent, dimethyl formamide (DMF) or the like, along with a catalyst and an organic base, preferably a tri(lower alkyl) amine such as triethylamine. The catalyst is selected so as to ensure that the coupling of the aldehyde or thioaldehyde moiety to the vinyl ketone or thioketone proceeds as desired; an exemplary catalyst is 3-benzyl-5-(2-hydroxyethyl)-4-methylthioazolium chloride. The reaction mixture is heated, preferably to at least about 50° C., more preferably to a temperature in the range of approximately 70° C. to 80° C., and the reaction is allowed to proceed. After cooling to room temperature, the reaction mixture is acidified with an inorganic acid such as hydrochloric acid. The product is then isolated; typically, the acidification step results in precipitation of the desired product (IV). This coupling reaction is exemplified in part (g) of the Example herein.

In the next step, the dione or dithione (IV) is reduced with a suitable reducing agent to give the diol or dithiol (V):

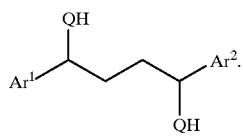
(V)

The reducing agent used to effect this reaction is, as will be appreciated by those skilled in the art, a compound which serves as a hydride donor, typically a metal hydride such as lithium aluminum hydride or sodium borohydride, with the latter agent preferred; see part (h) of the Example herein. The reaction is typically carried out in methanol, ethanol, or the like, and the reaction product may be used in the next step without purification.

Compound (V) is then caused to cyclize, to yield compound (VI).

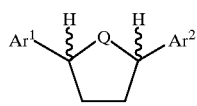
(VI)

The cyclization reaction is effected by heating the diol or dithiol (V), so that the reaction takes place at reflux. The reagents and conditions used are those which are typically used in the formation of cyclic ethers from diols; see, e.g., Schmoyer et al. (1960) *Nature* 187:592, which describes the preparation of tetrahydrofuran from 1,4-butanediol. As described in part (i) of the Example herein, the reaction may be carried out by admixing a solution of diol or dithiol (V) in benzene with orthophosphoric acid, heating to reflux, allowing the reaction to proceed to completion, and isolating the product from the organic solvent using conventional washing and extraction techniques.

The preceding step provides compound (VI) as a racemic mixture of cis and trans isomers. The racemate is then converted to the all-trans compound (I) by dissolving the racemate in a crystallization solvent, seeding the solvent with trans isomer, and cooling the mixture to promote crystallization. A particularly preferred crystallization solvent for this step is n-hexane.

In an important variation on this basic synthesis, either or both of the aromatic groups $Ar^1$ and $Ar^2$ are modified following cyclization and/or cis-trans isomerization. That is, in another embodiment of the invention, a process is provided for synthesizing a compound having the structural formula (Ia)

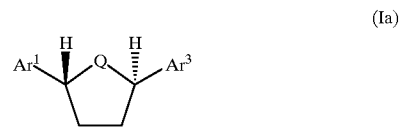
(Ia)

in which Q is O or S, $Ar^1$ is as defined above, and $Ar^3$ is as defined for $Ar^1$, the process comprising catalytically coupling an aldehyde or thioaldehyde (II)

(II)

to the vinyl ketone or thioketone (III)

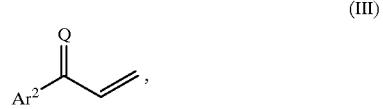
(III)

as described above, reducing the dione or dithione intermediate (IV) so provided to give the corresponding diol or dithiol (V), effecting cyclization to give the diaryl-substituted tetrahydrofuran or tetrahydrothiophene (VI)

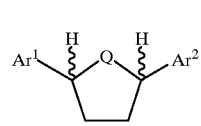
(VI)

as a racemic mixture of cis and trans isomers, chemically modifying $Ar^2$ to give $Ar^3$, thus providing compound (VIa)

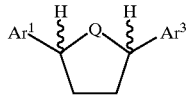
(VIa)

as a racemic mixture of cis and trans isomers, and effecting cis-trans isomerization in a suitable crystallization solvent, as explained above. Alternatively, $Ar^2$ may be converted to $Ar^3$ following cis-trans isomerization.

Preferably, in this embodiment, $Ar^1$ is

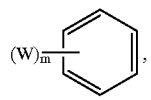

$Ar^2$ is

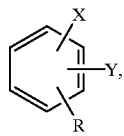

and $Ar^3$ is

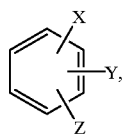

so that compound (Ia) is

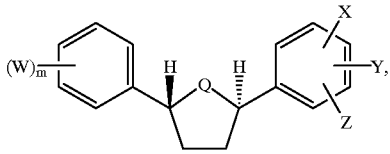

wherein:

the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W;

Y is

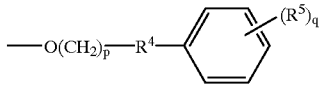

in which p is 2 or 3, q is 1, 2, 3 or 4, $R^4$ is S or $SO_2$, and $R^5$ is lower alkyl, lower alkoxy or halogen;

R is halogen or —COOR' wherein R' is lower alkyl; and

Z is

—O—$(CH_2)_r$—$NR^6$—(CO)N$\begin{matrix}R^7\\R^8\end{matrix}$ in which r is 0 or 1, $R^6$ is H or OH, $R^7$ is H or OH, and $R^8$ is lower alkyl.

More preferably, Q is O, $Ar^1$ is and $Ar^3$ is in which the * represent the points of binding and Hal is Cl or F. In this latter case, the compound synthesized has the structural formula

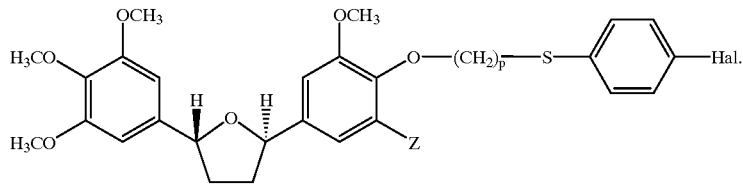

Specific compounds encompassed by this structural formula, which are preferred compounds to be synthesized using the present methodology, include (±) trans-2-[5-(N'-methyl-N'-hydroxyureidyl-methyl)-3-methoxy-4-p-chlorophenylthioethoxyphenyl]-5-(3,4,5-thrimethoxyphenyl)tetrahydrofuran, i.e., CMI-392

CMI-392

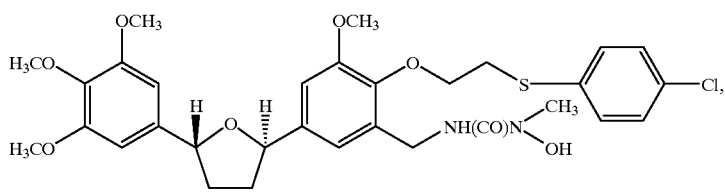

as well as variants thereof, particularly (±) trans-2-[5-(N'-methyl-N'-hydroxyureidylmethyl)-3-methoxy-4-p-chlorophenylthiopropoxyphenyl]-5-(3,4,5-trimethoxyphenyl)tetrahydrofuran, (±) trans-2-[5-(N'-methyl-N'-hydroxyureidylmethyl)-3-methoxy-4-p-fluorophenylthioethoxyphenyl]-5-(3,4,5-trimethoxyphenyl) tetrahydrofuran, and (±) trans-2-[5-(N'-methyl-N'-hydroxyureidylmethyl)-3-methoxy-4-p-fluorophenylthiopropoxyphenyl]-5-(3,4,5-trimethoxyphenyl)tetrahydrofuran, shown structurally as follows:

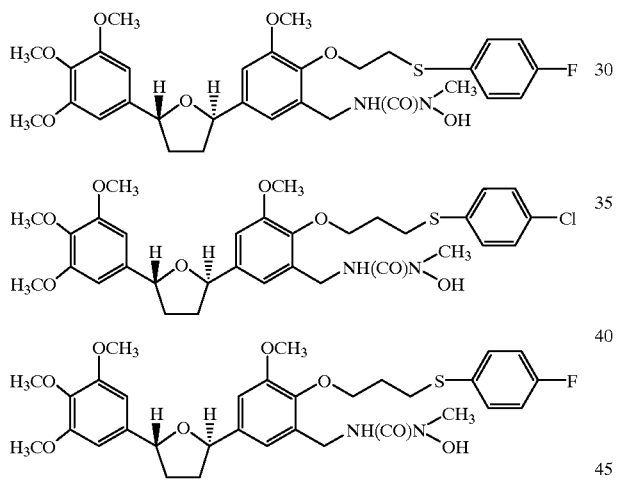

In another embodiment of the invention, processes are provided for preparing intermediates useful for synthesizing certain vinyl ketones or thioketones encompassed by structural formula (III). A key intermediate had the structural formula (VII)

(VII)

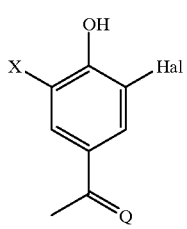

and is synthesized by treating the starting material (VIII)

(VIII)

with a halogenating reagent (Hal)$_2$ in the presence of a carbonate salt, at room temperature, followed by acidification of the reaction mixture. The reaction is exemplified in part (a) of the Example herein, using acetovanillone as a starting material and iodine as the halogenating reagent, thus providing 5-iodoacetovanillone as the product. In the above formulae, Hal is a halogen atom, Q is S or O, X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6. Preferably, Hal is I, Q is O, and X is methoxy.

Another important reaction for preparing an intermediate useful for synthesizing certain of the vinyl ketones and diketones encompassed by structural formula (III) involves preparation of a compound having the structural formula (IX)

(IX)

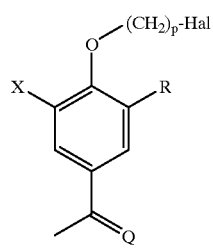

by treating the starting material (X)

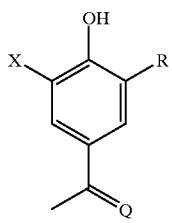

(X)

with a dihaloalkane Hal—(CH$_2$)$_p$—Hal at elevated temperature for a time sufficient to ensure complete reaction, wherein R is halogen or a lower alkyl ester —COOR' where R' is lower alkyl, the Hal are independently halogen, p is 2 or 3, Q is O or S, and X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6. Preferably, R is iodo or —COOCH$_3$, Q is O, and X is methoxy. The reaction is exemplified in part (c) of the Example, wherein 5- iodoacetovanillone is converted to 4-[2-bromoethoxy]-3-iodo-5-methoxy acetophenone.

In a further embodiment of the invention, a process is provided for preparing the vinyl ketone or thioketone (III)

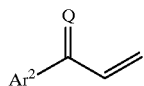

(III)

in which Q is O or S and Ar$^2$ is as defined above, i.e., Ar$^2$ is selected from the group consisting of aryl, aralkyl, heteroaryl and heteroaralkyl, optionally substituted with 1 to 3 substituents. The first step of the process involves treating the ketone or thioketone (XI)

(XI)

with paraformaldehyde and a halide salt of a di(lower alkyl)amine (R$^9$)$_2$NH$_2^+$Hal$^-$, in which R$^9$ is lower alkyl and Hal is a halogen atom, followed by treatment with an acid, to provide the Mannich salt (XII)

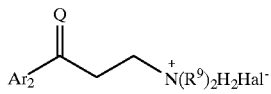

(XII)

The reaction conditions employed are those typically used in connection with carrying out the Mannich reaction; see, e.g., Scott et al. (1972) *J. Am. Chem. Soc.* 94:4779, Danishefsky et al. (1977) *J. Am. Chem. Soc.* 99:6066, and Wender et al. (1980) *J. Am. Chem. Soc.* 102:6340. Generally, the reaction is run in water, ethanol, isopropanol or acetic acid. The formaldehyde is introduced as is or in an aqueous solution. The amine, as noted above, is introduced as a halide salt, preferably as a hydrochloride salt. Reaction is preferably conducted at reflux for at least about 20 minutes. Preparation of a Mannich salt is exemplified in part (d) of the Example herein.

The Mannich salt (XII) is then quaternized, followed by elimination, as follows. The salt (XII) is dissolved in a basic solution, typically a sodium hydroxide solution, and extracted into an organic layer such as ethyl acetate or the like. The extracted product is then treated with a dialkyl or trialkyl halide, e.g., methyl iodide, and allowed to react for on the order of 5–6 hours. The quaternary ammonium salt (XIII)

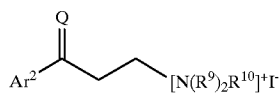

(XIII)

in which R$^{10}$ is hydrogen or alkyl, preferably lower alkyl, may be obtained by filtration and is then preferably air-dried prior to conducting the elimination reaction. Elimination is effected by heating an aqueous solution of the quaternary ammonium salt, adding a suitable solvent such as ethyl acetate, and extracting the desired product, i.e., the vinyl ketone or thioketone (III). Parts (e) and (f) of the Example herein exemplify quaternization of a Mannich salt followed by elimination.

Preferably, Ar$^2$ in the foregoing reaction has the structure

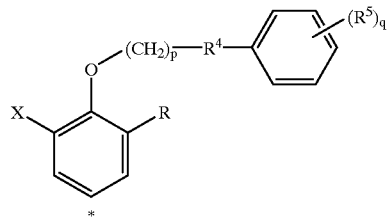

in which * represents the point of binding, p is 2 or 3, R$^4$ is S or SO$_2$, R$^5$ is lower alkyl, lower alkoxy or halogen, q is 1, 2, 3 or 4, R is halogen or a lower alkyl ester —COOR' where R' is lower alkyl, and X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, where R$^1$, R$^2$ and R$^3$ are independently hydrogen, alkyl or aryl, m is 1, 2 or 3, and n is an integer in the range of 1 to 6. More preferably, R is iodo or —COOCH$_3$, R$^4$ is S, R$^5$ is chloro or fluoro, and X is lower alkoxy.

In other embodiments of the invention, novel compounds are provided that may be isolated and identified in the foregoing syntheses, and that useful as starting materials and/or intermediates in the preparation of diaryl-substituted heterocycles. One of these compounds is compound (XIV), as follows:

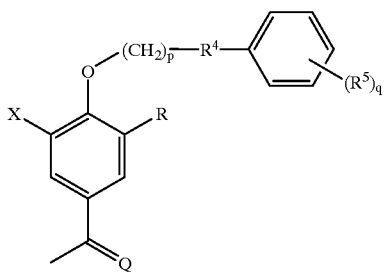

(XIV)

In compound (XIV):

X is selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

Q is O or S;

$R^4$ is S or $SO_2$;

$R^5$ is lower alkyl, lower alkoxy or halogen;

p is 2 or 3;

q is 1, 2, 3 or 4; and

R is halogen or a lower alkyl ester —COOR' where R' is lower alkyl.

Preferably: X is lower alkoxy; Q is O; $R^4$ is S; $R^5$ is halogen; q is 1; R is iodo or —$COOCH_3$. Most preferably, X is methoxy; and $R^5$ is Cl or F, and is in the para position.

Another novel compound useful as a starting material and/or intermediate in the synthesis of diaryl-substituted heterocycles, as described and claimed herein, has the structure of formula (XV):

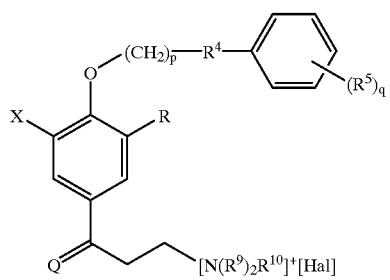

(XV)

In compound (XV):

X is selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

Q is O or S;

$R^4$ is S or $SO_2$;

$R^5$ is lower alkyl, lower alkoxy or halogen;

p is 2 or 3;

q is 1, 2, 3 or 4;

R is halogen or a lower alkyl ester —COOR' where R' is lower alkyl;

Hal is a halogen atom;

$R^9$ is lower alkyl; and $R^{10}$ is hydrogen or lower alkyl.

Preferably: X is lower alkoxy, Q is O; $R^4$ is S; $R^5$ is halogen; q is 1; R is iodo or —COOCH3; and Hal is iodo. More preferably, X is methoxy, $R^5$ is Cl or F, and is in the para position, $R^9$ is methyl or ethyl, and $R^{10}$ is hydrogen or $R^9$.

Another novel compound useful as a starting material and/or intermediated in the presently disclosed and claimed synthesis has the structural formula (XVI)

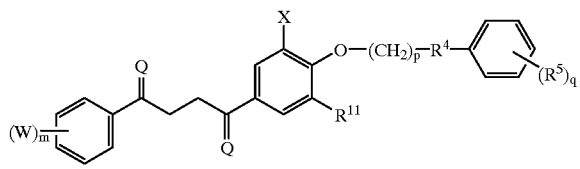

(XVI)

In compound (XVI):

the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W, m is 1, 2 or 3;

Q is O or S;

$R^4$ is S or $SO_2$;

$R^5$ is lower alkyl, lower alkoxy or halogen;

p is 2 or 3;

q is 1, 2, 3 or 4; and $R^{11}$ is a halogen atom, a lower alkyl ester —COOR' where R' is lower alkyl, or —CN.

Preferably: W and X are independently lower alkoxy; m is 3; Q is O; $R^4$ is S; $R^5$ is halogen; $R^{11}$ is iodo, —$COOCH_3$ or —CN; q is 1; and Hal is iodo. More preferably, W and X are methoxy, and $R^5$ is Cl or F, and is in the para position.

Another novel compound useful as a starting material and/or intermediate in the present syntheses has the structural formula (XVII)

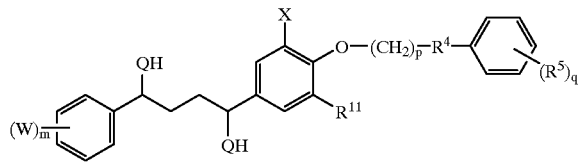

(XVII)

wherein:

the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W;

m is 1, 2 or 3;

Q is O or S;

$R^4$ is S or $SO_2$;

$R^5$ is lower alkyl, lower alkoxy or halogen;

p is 2 or 3;

q is 1, 2, 3 or 4; and $R^{11}$ is a halogen atom, a lower alkyl ester —COOR' where R' is lower alkyl, or —CN.

Preferably: W and X are independently lower alkoxy, m is 3; is O; $R^4$ is S; $R^5$ is halogen; q is 1; and $R^{11}$ is iodo, —$COOCH_3$ or —CN. More preferably, W and X are methoxy, and $R^5$ is Cl or F, and is in the para position.

An additional novel compound has the structural formula (XVIII)

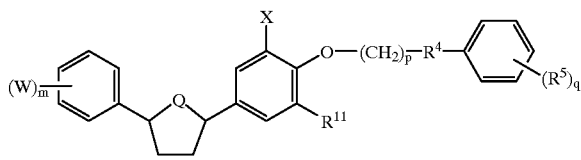

(XVIII)

wherein:
the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W;

m is 1, 2 or 3;

Q is O or S;

$R^4$ is S or $SO_2$;

$R^5$ is lower alkyl, lower alkoxy or halogen;

p is 2 or 3;

q is 1, 2, 3 or 4; and $R^{11}$ is a halogen atom, a lower alkyl ester —COOR' where R' is lower alkyl, or —CN.

Preferably: W and X are independently lower alkoxy; m is 3; Q is O; $R^4$ is S; $R^5$ is halogen; q is 1; and R is iodo, —$COOCH_3$ or —CN, More preferably, W and X are methoxy, $R^5$ is Cl or F, and is in the para position, and $R^{11}$ is iodo, —$COOCH_3$ or —CN.

Following synthesis of the diaryl-substituted heterocycle (I or Ia), the compound may be converted to a pharmaceutically acceptable salt, ester, amide, prodrug, or other derivative or analog or it may be modified by appending one or more appropriate functionalities to enhance selected biological properties. Such modifications are known in the art and include those which increase the rate of penetration into the skin or mucosal tissue, increase bioavalability, increase solubility, and the like. Conversion to salts, esters, amides, and the like may be carried out using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992).

The agents prepared using the presently disclosed and claimed synthetic techniques are useful for treating humans and other animals suffering from inflammatory and/or immune disorders, and, in particular, disorders mediated by PAF or products of 5-lipoxygenase, For example, the compositions find utility in the treatment in inflammatory skin disorders, including, but not limited to, psoriasis, contact dermatitis, atopic dermatitis (also known as allergic eczema), exfoliative dermatitis, seborrheic dematitis, erythemas (including erythema multiforme and erythema nodosum), discoid lupus erythematosus and dermatomyositis, The agents are particularly effective in treating psoriasis and atopic dematitis. The formulations are administered topically, as ointments, creams, gels, patches, or the like, as described in the preceding section, within the context of a dosing regimen effective to bring about the desired result.

It is to be understood that while the invention has been described in conjunction with the preferred specific embodiments thereof, the foregoing description, as well as the example which follows, are intended to illustrate and not limit the scope of the invention. Other aspects, advantages and modifications will be apparent to those skilled in the art to which the invention pertains.

The following example is put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All solvents were purchased as HPLC grade and, where appropriate, solvents and reagents were analyzed for purity using common techniques. All reactions were routinely conducted under an inert atmosphere of argon, unless otherwise indicated.

All patents, patent applications, and publications cited herein are incorporated by reference in their entireties.

EXAMPLE

Synthesis of CMI-392

Figure 1B:
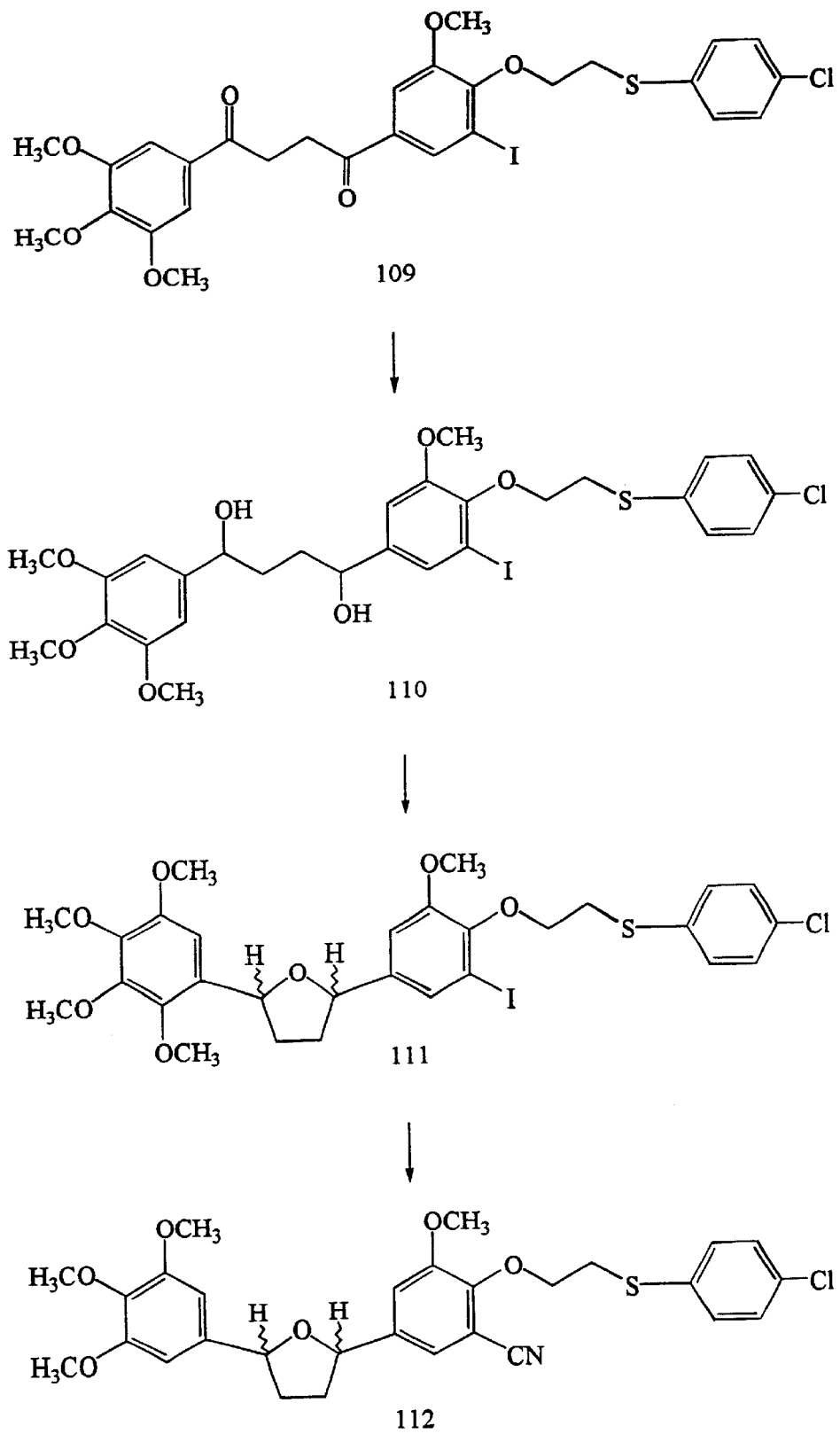
Figure 1C:
Figure 1C:
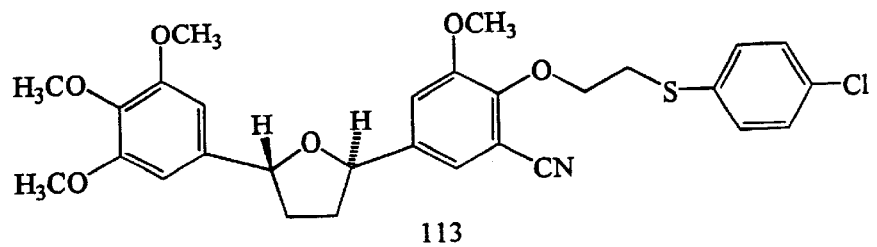
Figure 1C:
Figure 1C:
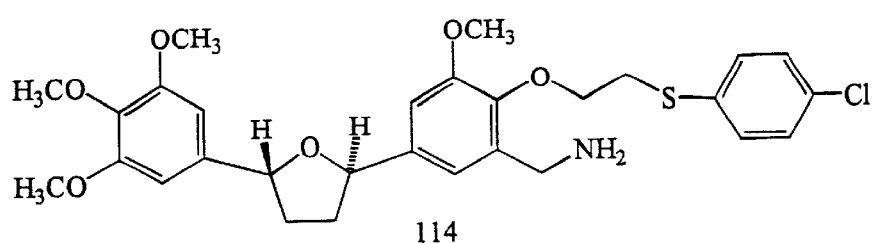
Figure 1C:
Figure 1C:
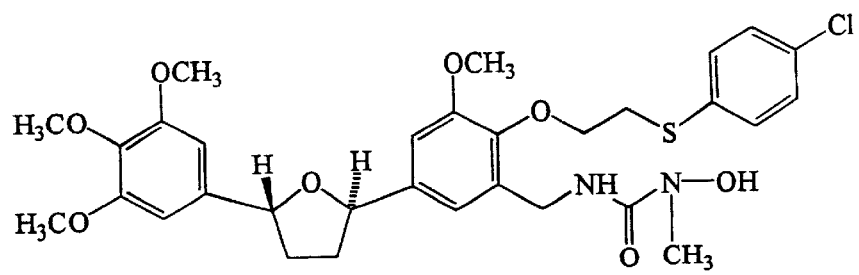
Figure 1C:
Figure 2A:
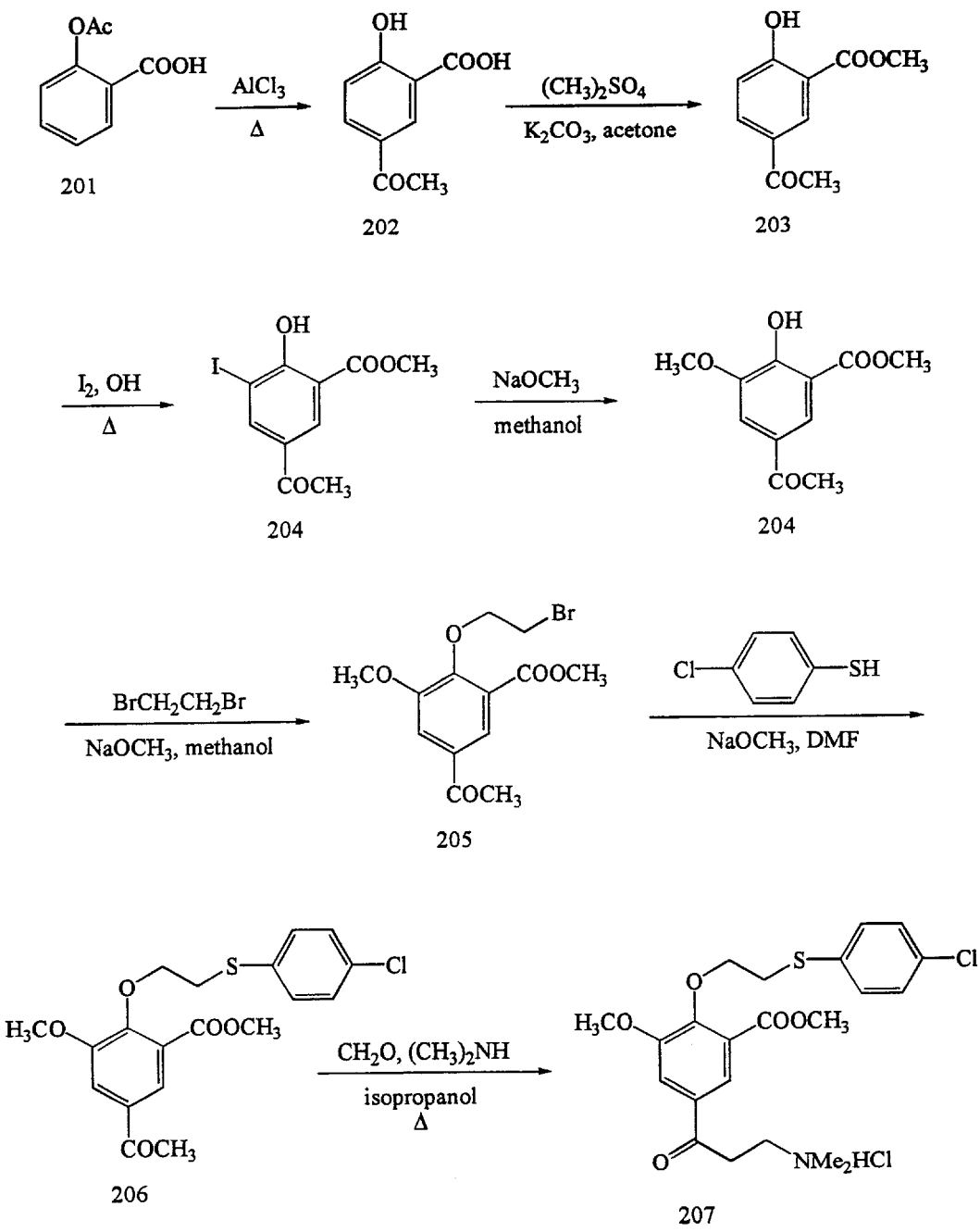
FIGS. 2a–2c schematically illustrate an alternative method for synthesizing crystalline CMI-392 using acetyl salicylic acid (aspirin) as a starting material.
Figure 2B:
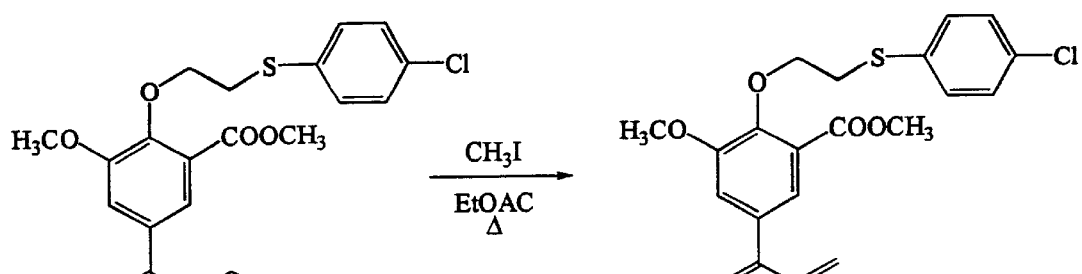
Figure 2B:
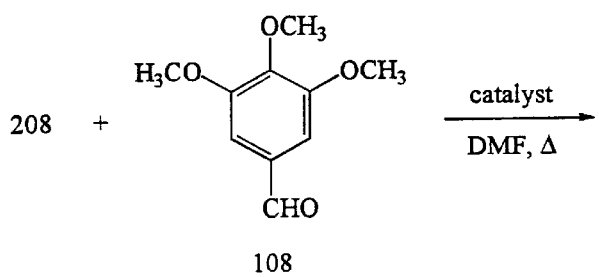
Figure 2B:
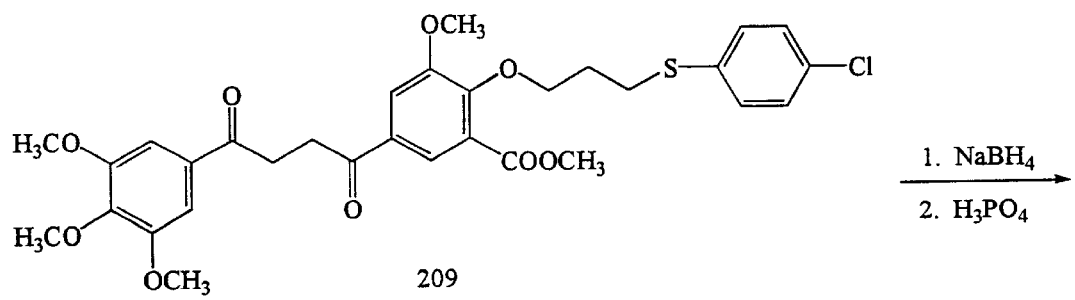
Figure 2B:
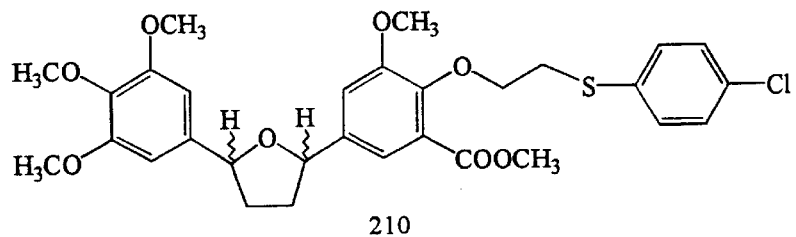
Figure 2C:
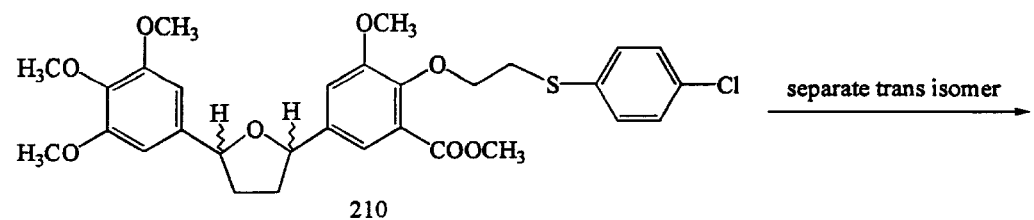
Figure 2C:
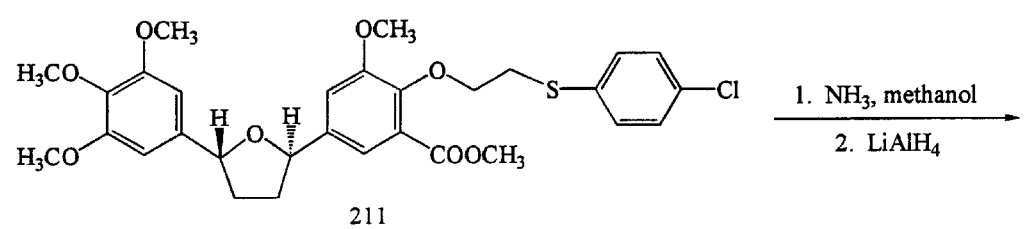
Figure 2C:
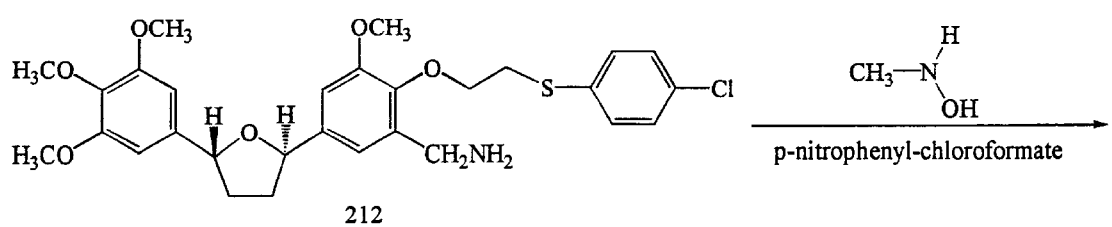
Figure 2C:
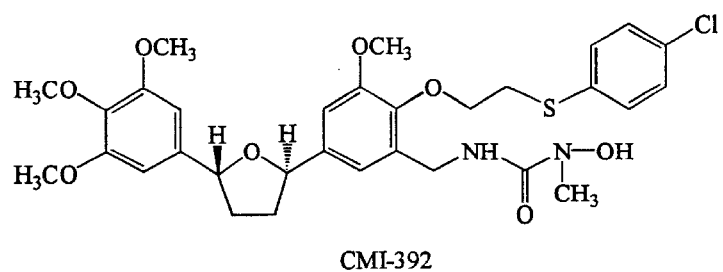

CMI-392, (±) trans-2-[5-(N'-methyl-N'-hydroxyureidylmethyl)-3-methoxy4-p-chlorophenylthioethoxyphenyl]-5-(3,4,5-trimethoxyphenyl)-tetrahydrofuran, was prepared using the synthesis shown in FIGS. 1a through 1c, as follows:

(a) 5-Iodoacetovanillone (compound 102): Sodium hydrogen carbonate (657 g) was dissolved in water (8 L), acetovanillone (1.0 kg) was then added and the solution stirred for 0.5 hours, Iodine (1.828 kg) was added in 10–15 g portions over a period of 2 hours, and the reaction mixture was stirred for 18–20 hours at room temperature. The reaction was monitored by TLC (silica gel, solvent system: benzene). The reaction solution was acidified with concentrated HCl (175 ml) bringing the pH to about 2, and the solution stirred for an additional hour. The solid was collected by filtration, washed with 20% sodium dithionite solution (5 L) and water (5 L), and dried for 12–14 hours at room temperature. The crude product was crystallized from isopropyl alcohol (2 L). Yield: 1.51 kg (85%), purity: 91% (HPLC), m.p.: 175–176° C.

(b) 4-[2-Bromoethoxy]-3-iodo-5-methoxyacetophenone (compound 103): To a 10 L three neck round bottom flash containing 5-iodovanillone (compound 102, 1.0 kg) dissolved in DMF (5 L) containing potassium carbonate (1.417 kg), was added 1,2-dibromoethane (2.57 kg). The solution was heated to 60–70° C. for 4–5 hours. The reaction was monitored by TLC (silica gel, solvent system: 30% ethyl acetate in n-hexane). The solution was cooled to room temperature and the solid collected by filtration and washed with benzene (500 mL). The filtrate was concentrated under reduced pressure. The residue was dissolved in benzene (3 L), washed with water (2×1 L) and saturated brine solution (2×1 L). The organic layer was dried over sodium sulfate (500 g) and concentrated under reduced pressure to give compound. Yield: 1.025 kg (75%), purity: 87% (HPLC), m.p.: 82–83° C.

(c) 3-Iodo-5-methoxy-4-[2-p-chlorothiophenylethoxy] acetophenone (compound 104): A 10 L three neck round bottom flask fitted with a calcium chloride guard tube and containing THF (2.5 L) was cooled to 0–5° C. and sodium methoxide (149 g) was slowly added over a 1 hour period. A solution of 0.362 kg p-chlorothiophenol in 1.0 L THF was then added over a 1-hr. period. The solution was stirred for another 1.5 hours at below 10° C., and then compound 103 (1.0 kg) in THF (1.5 L) was slowly added over a 1.5 hour period. The reaction was stirred at room temperature for 12–14 hours and monitored by TLC (silica gel, solvent system: 25% benzene in hexane). Saturated ammonium chloride (500 mL) was then added, the solution stirred for 1 hour, and the organic layer was separated and concentrated under reduced pressure. The residue was washed with water (2×2 L) and dried at room temperature for 24 hours. Yield: 1.08 kg (93%), purity: 90%, m.p.: 100–101° C.

(d) Mannich salt of 3-iodo-5-methoxy-4-[2-p-chlorothiophenylethoxy]acetophenone (compound 105): In a 5 L flask filter with a calcium chloride guard tube, compound 104 (500 g), paraformaldehyde (32 g), dimethylamine HCl (76 g) and concentrated HCl (20 mL) were combined and the contents refluxed for 2 hours. The reaction was monitored by TLC (silica gel, solvent system: 25% benzene in n-hexane). Paraformaldehyde (32 g) and dimethylamine HCl (76 g) were added to the reaction mixture twice, followed by reflux for 2 hours after each addition. The reaction was allowed to cool to room temperature, acetone 1.5 L) was added, and the reaction cooled to 0° C. for 4–5 hours. The solid was collected by filtration, washed with acetone (500 mL), and dried at room temperature for 2–3 hours. Yield: 325 g (54%), m.p.: 142–144° C.

(e) Quaternary ammonium salt of 3-iodo-5-methoxy-4-[2-p-chlorothiophenylethoxy]acetophenone (compound 306): Compound 305 (304 g) was dissolved in ethyl acetate (1.0 L) and then 3.5% solution of NAOH (1 L) was added. The reaction mixture was stirred for 0.5 hours, the organic layer was separated, and the aqueous layer extracted with ethyl acetate (2×250 mL). The organic layers were combined, washed with water (2×500 mL) and dried over sodium sulfate. The inorganic salts were separated by filtration. The organic filtrate was cooled to 0° C. in a 3 L round bottom flask and then methyl iodide (106 g) was added in three portions over 0.5 hours. The reaction mixture was then stirred at room temperature for 5–6 hours. The solid was collected by filtration and washed with ethyl acetate (500 mL). Yield: 310 g (81%), m.p.: 135–137° C.

(f) 3-Iodo-5-methoxy4-(2-p-chlorothiophenylethoxy) phenyl vinyl ketone (compound 107): In a 5 L round bottom flask, compound 106 (300 g) was added to water (1.5 L) that was warmed to 35–40° C., Then, ethyl acetate (1.0 L) was added and the reaction solution refluxed for 1 hour. Upon cooling to room temperature, the organic layer was separated, and the aqueous layer was again refluxed with ethyl acetate (2×250 mL). The combined organic layers were dried over sodium sulfate and concentrated under reduced pressure. Yield: 186 g (86%), purity: 95% (HPLC), m.p.: 91–92°C.

(g) 1-(3', 4', 5'-Trimethoxyphenyl)4-[3"-iodo-5"-methoxy-4"-(2-p-chlorothiophenyl-ethoxy)phenyl]-1,4-dioxobutane (compound 109): 3-Benzyl-5-(2-hydroxyethyl)-4-methyl-thiazolium chloride catalyst (45.5 g) and 3,4,5-trimethoxybenzaldehyde (compound 108, 165 g) were dissolved with stirring in DMR (1 L) in a 5 L round bottom flask containing a calcium chloride guard, and then compound (307) (400 g) was added. After about 0.5 hours of stirring, trimethylamine (128 g) was slowly added and the reaction mixture heated to 70–80° C. until completion as determined by TLC (silica gel, solvent system: 40% ethyl acetate in n-hexane). The reaction mixture was then cooled to room temperature and 10% HCl (4 L) was added slowly with vigorous stirring for about 1 hour. The aqueous layer was decanted, and the product washed with water (2×2 L) with decantation. The crude product was stirred in isopropyl alcohol (1 L) for 1 hour, the solid collected by filtration and washed with isopropyl alcohol (500 mL). Yield: 425 g (75.2% ), m.p.: 105–107° C.

(h) 1-[3'-Iodo-5'-methoxy-4'-(2-p-chlorothiophenylethoxy)phenyl-4-(3 ",4",5"-trimethoxyphenyl)-butan-1,4-diol (compound 110): Compound 109 (400 g) was dissolved in THF (2 L) and methanol (100 mL), and the 5 L round bottom flask was cooled to 0° C. NABH$_4$ (25 g) was then added in 2–3 g portions over a period of 1 hour. Stirring was continued for 2 hours at below 10° C. The reaction was then quenched with a saturated solution of ammonium chloride (100 mL) and stirred for another hour. The solvents were removed under reduced pressure, benzene (1.5 L) and water (1.0 L) were added to the residue, the organic layer was separated and the aqueous layer was extracted once again with benzene (0.5 L). The combined organic layers were washed with water (0.5 L) and then with brine (2×0.5 L), dried over sodium sulfate and filtered. The compound in the filtrate was used in the next step without further purification.

(i) Cis/trans-2-(3',4',5'-Trimethoxyphenyl)-5-[3"-iodo-5"-methoxy-4-(2-p-chlorothiophenylethoxy)phenyl]

tetrahydrofuran (compound 111). The benzene solution containing compound 110 (2 L), prepared in the preceding step, and orthophosphoric acid (130 mL) were placed in a 3 L round bottom flask and refluxed for 2 hours. The contents were cooled to room temperature and the upper benzene layer was decanted. The benzene layer was washed with water (500 mL), 20% sodium bicarbonate (2×500 mL) and finally with brine (2×500 mL). The organic layer was dried over sodium sulfate and concentrated under reduced pressure to give an oily compound, Yield: 370 g (94%).

(j) Cis/trans-2-(3',4',5'-Trimethoxyphenyl)-5-[3'-cyano-5"-methoxy-4"-(2-p-chlorothiophenylethoxy)phenyltetrahydrofuran (compound 112). In a 3 L round bottom flask, compound (111) (370 g) was dissolved in DMF (900 mL), cuprous cyanide (75.7 g) was then added in one portion, and the reaction mixture was heated to 120–125° C. for 4–5 hours. The reaction was monitored by TLC (silica gel, solvent system: 30% ethyl acetate in n-hexane). The mixture was cooled to room temperature, water (4 L) and benzene (1 L) were added, and the solid was filtered and washed with benzene (500 mL). The organic layer was separated and washed with water (500 mL), brine (2×500 mL), dried over sodium sulfate, and filtered through a silica gel bed. Benzene solution was concentrated under reduced pressure, and the residue used in the next step without further purification. Yield: 230 g (73.4%).

(k) Crystallization of the cis-trans mixture of compound 112 to give pure trans compound 113: The cis-trans mixture of compound 112 (230 g) was dissolved in ethyl (1 L) and n-hexane (900 mL) was slowly added with stirring until turbidity of the solution persisted. The solution was cooled to room temperature, then seeded with pure trans compound, and left standing at −10° C. for 10–12 hours. The white solid was filtered and washed with 20% ethyl acetate in n-hexane four times. The white product was washed with n-hexane (100 mL) and dried under vacuum for 2 hours.

The organic layers were combined and concentrated under reduced pressure. The residue (150 g) was dissolved in chloroform (270 mL) and trifluoroacetic acid (30 mL) was added. The mixture was stirred for 7–8 hours at room temperature. Water (200 mL) was added and the organic layer separated, washed with water (200 mL), 20% sodium bicarbonate solution (200 mL) and finally with brine (200 mL), and dried over sodium sulfate. Chloroform was removed under reduced pressure. The residue was dissolved in ethyl acetate (220 mL) and hexane (500 mL) was added with stirring until turbidity persisted. As above, the solution was seeded with pure trans compound, and left standing at −10°C. for 12–14 hours. The solid was collected by filtration, washed four times with 20% ethyl acetate in n-hexane, and added under vacuum for 2 hours. The solid thus obtained was thoroughly mixed with the first solid, the mixture suspended in hexane (150 mL), filtered, and added. Yield: 105 g (45.6%), purity: 97% trans, 1.2% cis, m.p.: 85–86° C.

(l) Trans-2-(3'4', 5'-Trimethoxyphenyl)-5-[3'-aminomethyl-5"-methoxy-4"-(2-p-chlorothiophenylethoxy)phenyl]tetrahydrofuran (compound 114). Compound 113 (100 g) was dissolved in THF (500 mL) and cooled to 0° C. in a 2 L round bottom flask. Then alane-N,N-dimethylethylamine complex in toluene (0.5 K 800 mL) was slowly added under a N$_2$ atmosphere. The reaction mixture was then refluxed for 2 hours, stirred at room temperature for 1 hour, and then cooled to 0° C. The reaction was quenched with saturated sodium chloride solution (50 mL), the solid collected by filtration, and washed with hot THF (2×100 mL). The combined filtrate and washings were concentrated under reduced pressure. To the residue obtained, toluene (100 mL) was added and then removed under reduced pressure to give a thick oil. Yield: 95.6 g (95%).

(m) CMI-392, (±) trans-2-[5-(N'-methyl-N'-hydroxyureidylmethyl)-3-methoxy-4-p-chlorophenylthioethoxyphenyl]-5-(3,4,5-trimethoxyphenyl)tetrahydrofuran: To a 2 L round bottom flask containing toluene (400 mL) cooled to 0° C. was added p-nitrophenylchloroformate (36 g). Then, compound 114 (95 g) dissolved in toluene (400 mL) was slowly added followed by trimethylamine (18 g). The reaction mixture was stirred at 0° C. for 2.5 hours. In a separate flask, to N-methylhydroxylamine HCl (21.3 g) in DCM (200 mL) was added trimethylamine (27 g). The resultant mixture was added to the reaction vessel above along with trimethylamine (18 g). The reaction mixture was heated to 60–65° C. for 3 hours, and monitored by TLC (silica gel, solvent system: 60% ethyl acetate in hexane). The reaction mixture was cooled to room temperature, water (500 mL) was then added, and the organic layer was separated and washed with 10% potassium hydrogen sulfate (1×300 mL, 2×150 mL), 1N NaOH solution (800 mL), brine (4×250 mL), 10% potassium hydrogen sulfate solution (200 mL) and finally with brine (500 mL). The organic layer was dfied over sodium sulfate and concentrated to give an oil. Yield: 105 g (98%).

(n) Purification of CM-392: The oily product obtained in the preceding step was dissolved in isopropyl alcohol (300 mL) by warming to 45–50° C. The solution was then cooled to −10° C. for 12 hours. To the cold solution, n-hexane (300 mL) was added, seeded with pure CMI-392, and left below −10° C. for another 10–12 hours. The solid was collected by filtration, washed with 5% isopropyl alcohol in n-hexane (100 mL) and dried. The product was recrystallized from isopropyl alcohol in hexane (1:1) as above, and washed with 10% isopropyl alcohol in n-hexane (4× 150 mL). The compound was then suspended in n-hexane (100 mL), filtered, and dried under vacuum for 2 hours. Yield: 70 g (67%), purity: 98% (HPLC), m.p.: 54–55° C.

What is claimed is:
1. A process for preparing a compound having the structural formula (I)

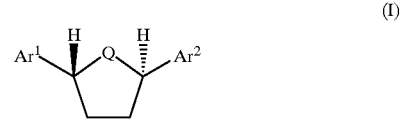

(I)

in which Ar$^1$ and Ar$^2$ are selected from the group consisting of aryl, aralkyl, heteroaryl and heteroaralkyl, optionally substituted with 1 to 3 substituents, and Q is O or S, the process comprising:

(a) catalytically coupling a compound having the structure (II)

(II)

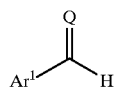

to a compound having the structure (III)

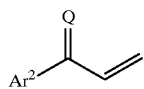

under reaction conditions effective to produce the diaryl-substituted dione or dithione intermediate (IV)

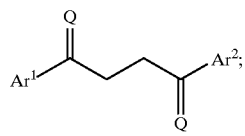

(b) treating compound with a reducing agent, thereby providing compound (V)

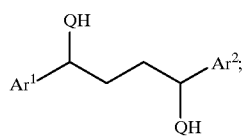

(c) effecting cyclization of compound (V), under acidic conditions, to produce cyclized intermediate (VI)

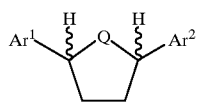

as a racemic mixture of cis and trans isomers; and (d) isomerizing the cis isomer in the racemic mixture to give the trans isomer by dissolving the racemic mixture in a crystallization solvent, seeding the solvent with trans isomer, and cooling the mixture to promote crystallization, thereby effecting cis-trans isomerization.

2. The process of claim 1, wherein Q is O.

3. The process of claim 1, wherein Q is S.

4. The process of claim 1, wherein $Ar^1$ and $Ar^2$ are independently selected from the group consisting of phenyl and pyridinyl, either unsubstituted or substituted at least one substituent selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6.

5. The process of claim 1, further comprising, after either or both of step (c) and step (d), chemically modifying $Ar^1$, $Ar^2$, or both $Ar^1$ and $Ar^2$ to produce $Ar^3$ and where $Ar^3$ is as defined for $Ar^1$.

6. A process for preparing a compound having the structural formula (Ia)

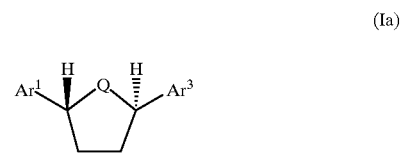

in which $Ar^1$ and $Ar^3$ are selected from the group consisting of aryl, aralkyl, heteroaryl and heteroaralkyl, substituted with 1 to 3 substituents, and Q is O or S, the process comprising:

(a) catalytically coupling a compound having the structure (II)

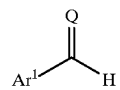

to a compound having the structure (III)

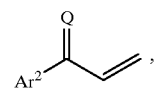

in which $Ar^2$ is defined as for $Ar^1$ and $Ar^3$, under conditions effective to produce the diaryl-substituted dione or dithione intermediate (IV)

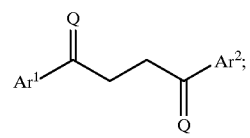

(b) treating compound (IV) with a reducing agent, thereby providing compound (V)

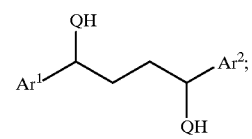

(c) effecting cyclization of compound (V), under acidic conditions, to produce cyclized intermediate (VI)

(VI)

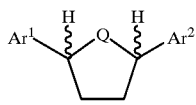

as a racemic mixture of cis and trans isomers;
(d) chemically modifying Ar² to give Ar³, thus providing compound (VIa)

(VIa)

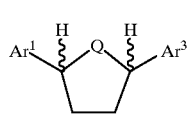

as a racemic mixture of cis and trans isomers; and
(e) isomerizing the cis isomer in the racemic mixture of (VIa) to give the trans isomer by dissolving the racemic mixture of (VIa) in a crystallization solvent seeding the solvent with trans (VIa), and cooling the mixture to promote crystallization, thereby effecting cis-trans isomerization.

7. The process of claim 6, wherein Ar¹ is

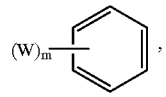

Ar² is

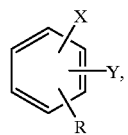

and Ar³ is

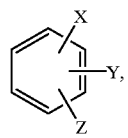

so that compound (Ia) is

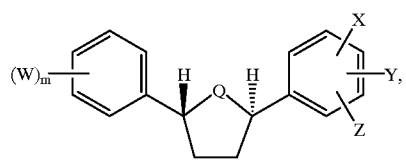

wherein:
the W are independently selected from the group consisting of alkyl, alkenyl, alkynyl, halogen, halogenated alkyl, halogenated alkenyl, halogenated alkynyl, $-OR^1$, $-(CH_2)_nOR^1$, $-O(CH_2)_n-OR^1$, $-SR^1$, $-(CH_2)_nSR^1$, $-S(CH_2)_nSR^1$, $-COOR^1$, $-(CO)R^1$, $-NR^2R^3$, $-(CO)NR^2R^3$, $-O(CO)NR^2R^3$, and $-CN$, wherein $R^1$, $R^2$ and $R^3$ are independently hydrogen, alkyl or aryl m is 1, 2 or 3, and n is an integer in the range of 1 to 6;

X is defined as for W;

Y is

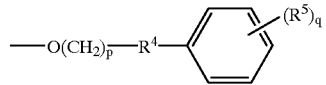

in which p is 2 or 3, q is 1, 2, 3 or 4, $R^4$ is S or $SO_2$, and $R^5$ is lower alkyl, lower alkoxy or halogen;

R is halogen or $-COOR'$ wherein R' is lower alkyl; and

Z is

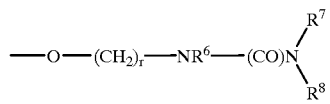

in which r is 0 or 1, $R^6$ is H or OH, $R^7$ is H or OH, and $R^8$ is lower alkyl.

8. The process of claim 7, wherein Q is O, Ar¹ is

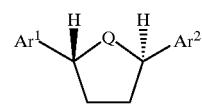 and

Ar³ is in which the * represent the points of binding and Hal is Cl or F.

9. A process for preparing a compound having the structural formula (I)

(I)

in which Ar¹ and Ar² are selected from the group consisting of aryl, aralkyl, heteroaryl and heteroaralkyl, optionally substituted with 1 to 3 substituents, and Q is O or S, the process comprising:

(a) treating the diaryl-substituted dione or dithione (IV)

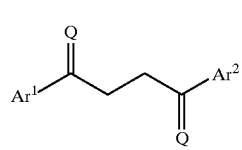
(IV)

with a reducing agent thereby providing compound (V)

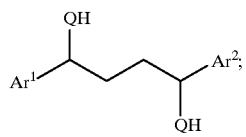
(V)

(b) effecting cyclization of compound (V), under acidic conditions, to produce cyclized intermediate (VI)

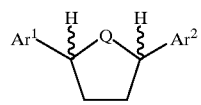
(VI)

as a racemic mixture of cis and trans isomers; and
(c) isomerizing the cis isomer in the racemic mixture to give the trans isomer by dissolving the racemic in a crystallization solvent, seeding the solvent with trans isomer, and cooling the mixture to promote crystallization, thereby effecting cis-trans isomerization.

10. The process of claim 9, wherein Q is O.

11. The process of claim 9, wherein Q is S.

12. The process of claim 9, wherein $Ar^1$ and $Ar^2$ are independently selected from the group consisting of phenyl and pyridinyl, either unsubstituted or substituted at least one substituent selected from the group consisting of alkyl, alkenyl, alkynyl, halogen, halogenated alkyl, halogenated alkenyl, halogenated alkynyl, —$OR^1$, —$(C_2)_n OR^1$, —$O(CH_2)_n OR^1$, —$SR^1$, —$(CH_2)_n$, $SR^1 m$ —$S(CH_2)_n SR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl m is 1, 2 or 3, and n is an integer range of 1 to 6.

13. The process of claim 9, further comprising, after either or both of step (b) and step (c), chemically modifying $Ar^1$, $Ar^2$, or both $Ar^1$ and $Ar^2$ to produce $Ar^3$ and where $Ar^3$ is as defined for $Ar^1$.

14. A process for preparing a compound having the structural formula (Ia)

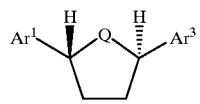
(Ia)

in which $Ar^1$ and $Ar^3$ are selected from the group consisting of aryl, aralkyl, heteroaryl and heteroaralkyl, substituted with 1 to 3 substituents, and Q is O or S, the process comprising:

(a) treating the diaryl-substituted dione or dithione (IV)

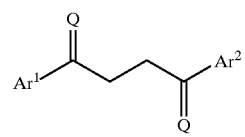
(IV)

in which $Ar^2$ is defined as for $Ar^1$ and $Ar^3$, with a reducing agent, thereby providing compound (V)

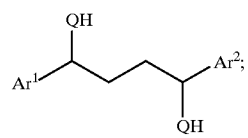
(V)

(b) effecting cyclization of compound (V), under acidic conditions, to produce cyclized intermediate (VI)

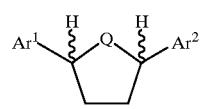
(VI)

as a racemic mixture of cis and trans isomers;
(c) chemically modifying $Ar^2$ to give $Ar^3$, thus providing compound (VIa)

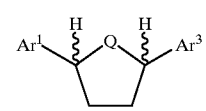
(VIa)

as a racemic mixture of cis and trans isomers; and
(d) isomerizing the cis isomer in the racemic mixture of (VIIa) to give the trans isomer by dissolving the racemic mixture of (VIa) in a crystallization solvent, seeding the solvent with trans (VIa), and cooling the mixture to promote crystallization, thereby effecting cis-trans isomerization.

15. The process of claim 14, wherein $Ar^1$ is

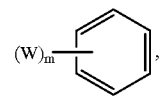

$Ar^2$ is

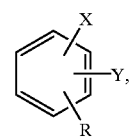

and Ar³ is

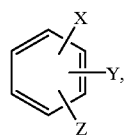

so that compound (Ia) is

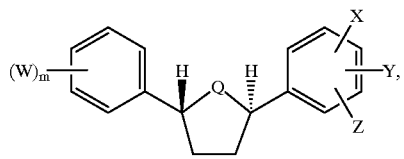

wherein:
the W are independently selected from the group consisting of alkyl, alkenyl, alkynyl, halogen, halogenated alkyl, halogenated alkenyl, halogenated alkynyl, $-OR^1$, $-(CH_2)_nOR^1$, $-O(CH_2)_nOR^1$, $-SR^1$, $-(CH_2)_nSR^1$, $-COOR^1$, $-(CO)R^1$, $-NR^2R^3$, $-(CO)N^2R^3R$, $-O(CO)NR^2R^3$, and $-CN$, wherein $R^1$, $R^2$ and $R^3$ are independently hydrogen, or m is 1, 2 or 3, and n is an integer in the range of 1 to 6;
X is defined as for W;
Y is

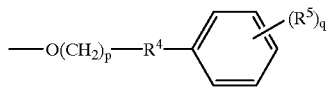

in which p is 2 or 3, q is 1, 2, 3 or 4, $R^4$ is S or $SO_2$, and $R^5$ is lower alkyl, lower alkoxy or halogen;

R is halogen or $-COOR'$ wherein R' is lower alkyl, and Z is

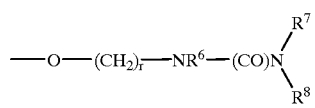

in which r is 0 or 1, $R^6$ is H or OH, $R^7$ is H or OH, and $R^8$ is lower alkyl.

16. The process of claim 15, wherein Q is O, Ar¹ is

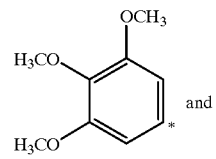

and

Ar³ is

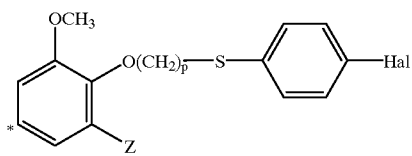

in which the * represent points of binding and Hal is Cl or F.

* * * * *